(12) United States Patent
Nakakubo

(10) Patent No.: US 8,211,586 B2
(45) Date of Patent: Jul. 3, 2012

(54) COMBUSTIBLE GAS DETECTOR, PROCESS FOR PRODUCING COMBUSTIBLE GAS DETECTOR, AND FUEL CELL SYSTEM EQUIPPED WITH COMBUSTIBLE GAS DETECTOR

(75) Inventor: Toru Nakakubo, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 1341 days.

(21) Appl. No.: 11/828,693

(22) Filed: Jul. 26, 2007

(65) Prior Publication Data
US 2008/0038590 A1    Feb. 14, 2008

(30) Foreign Application Priority Data
Aug. 9, 2006   (JP) ................................. 2006-216472

(51) Int. Cl.
*H01M 8/00* (2006.01)
(52) U.S. Cl. ......................................... 429/468; 422/94
(58) Field of Classification Search ..................... 429/22, 429/428, 502, 524, 535; 73/204.11; 422/94; 427/123
See application file for complete search history.

(56) References Cited

U.S. PATENT DOCUMENTS

| | | | |
|---|---|---|---|
| 6,384,509 B1 | 5/2002 | Tomonari et al. | |
| 6,640,626 B2 * | 11/2003 | Saikalis et al. | 73/204.11 |
| 6,791,233 B2 | 9/2004 | Tomonari et al. | |
| 7,309,022 B2 | 12/2007 | Nakakubo | |
| 2003/0056570 A1 | 3/2003 | Shin et al. | |
| 2007/0026275 A1 * | 2/2007 | Sasaki et al. | 429/22 |
| 2007/0212263 A1 | 9/2007 | Shin et al. | |
| 2008/0303532 A1 | 12/2008 | Nakakubo et al. | |
| 2009/0053580 A1 | 2/2009 | Morita et al. | |

FOREIGN PATENT DOCUMENTS

| | | |
|---|---|---|
| JP | 44-11960 Y1 | 5/1969 |
| JP | 8-508571 A | 9/1996 |
| JP | 8-315847 A | 11/1996 |
| JP | 2000-246676 A | 9/2000 |
| JP | 2003-156461 A | 5/2003 |
| JP | 2005-300522 A | 10/2005 |
| JP | 2005-326269 A | 11/2005 |
| WO | 95/02180 A1 | 1/1995 |

OTHER PUBLICATIONS

Office Action in Japanese Application No. 2006-216472 (Jul. 2011).
D.R. Baselt et al., "Design and Performance of a Microcantilever-Based Hydrogen Sensor," B88 Sensors and Actuators 120-31 (2003) (no month).
Hal Jerman, "Electrically-Activated, Normally-Closed Diaphragm Valves," 4 J. Micromech. Microeng. 210-16 (no month 1994).
S. Timoshenko, "Analysis of Bi-Metal Thermostats," 11 J. Opt. Soc. Am. 233-55 (Sep. 1925).

* cited by examiner

*Primary Examiner* — Jennifer Michener
*Assistant Examiner* — Monique Wills
(74) *Attorney, Agent, or Firm* — Fitzpatrick, Cella, Harper & Scinto

(57) ABSTRACT

A combustible gas detector, which has low power consumption, low-noise and high-speed response and which enable miniaturization, a process for producing the combustible gas detector, and a fuel cell system equipped with a combustible gas detector are provided. The combustible gas detector for detecting a combustible gas includes a catalyst for reaction with the combustible gas, a first displacement unit including a flexible member, which is displaced with catalytic combustion by the reaction of the catalyst with the combustible gas, and electrical contacts, which are switched by the displacement of the flexible member in the first displacement unit.

15 Claims, 17 Drawing Sheets

COMBUSTIBLE GAS DETECTOR, PROCESS FOR PRODUCING COMBUSTIBLE GAS DETECTOR, AND FUEL CELL SYSTEM EQUIPPED WITH COMBUSTIBLE GAS DETECTOR

BACKGROUND OF THE INVENTION

1. Field of the Invention

The present invention relates to a combustible gas detector for detecting a combustible gas, a process for producing the combustible gas detector, and a fuel cell system equipped with the combustible gas detector.

2. Description of the Related Art

As the development of hydrogen utilization technology such as fuel cells advances, the importance of combustible gas sensors increases so as to more safely control these systems.

For example, it is known that hydrogen explodes if it is present at a concentration of 4 to 75% in the air. If a combustible gas leaks to the outside due to a system failure or when a purging (scavenging) operation is necessary for driving the system, it is necessary to keep an ignition source away from the explosible concentration area. Recently, there has been a demand not only for the development of in-car and at-home stationary types of fuel cells, but also for the development of small-size fuel cells for mobile devices as a substitute for conventional secondary batteries advances. Furthermore, there is a demand for miniaturization and low power consumption of combustible gas sensors.

Conventionally, various types of combustible gas sensors have been developed and marketed. These are roughly classified into three types, that is, an adsorption type, a catalytic combustion type, and a gas heat conduction type. These sensors are used respectively depending on a gaseous species, a detection region, or response speed. Of these, the adsorption-type combustible gas sensor measures the change of electric resistance or volume expansion when a gas is adsorbed onto the surface of a metal oxide semiconductor (tin oxide) or the like. The catalytic combustion-type combustible gas sensor measures the change in resistance associated with the increase in temperature caused by catalytic combustion of a gas at the surface of a catalyst (platinum line or the like). The gas heat conduction-type combustible gas sensor measures the change in the electric resistance associated with the change in the temperature of a heating element (platinum coil or the like) by the difference in the specific thermal conductivity of a gas.

The development adopting semiconductor processing technique has been hitherto advanced to achieve miniaturization and low power consumption of these combustible gas sensors. The semiconductor processing technique is a fine processing technique for manufacturing LSI using a material such as a silicon wafer. A so-called MEMS (micro-electro-mechanical systems) technique has been extensively developed and already put into practical use in the production of acceleration sensors for automobiles.

D. R. Baselt et al., Sensors and Actuators B88 (2003) 120-131 provides an example of miniaturizing a combustible gas sensor using a semiconductor processing technique. This sensor is an adsorption type sensor in which a palladium film is formed on a cantilever made of Si. In this sensor, when a combustible gas is adsorbed to the palladium film, the film expands and deflects the cantilever. This deflection is detected by the change of the capacitance between the electrode on the cantilever and the electrode on the substrate.

As a catalytic combustion-type combustible gas sensor, sensors provided with a catalyst material and a thermoelectric conversion element at the same time are proposed as shown, for example, in Japanese Patent Application Laid-Open No. 2003-156461. In this sensor, heat generated by the catalytic reaction between a combustible gas and the catalyst material is converted into a voltage signal by a thermoelectric conversion effect, and this is used as a detection signal. Furthermore, Japanese Patent Application Laid-Open No. 2005-300522 discloses technology for further miniaturizing such a sensor using a semiconductor processing technique.

When hydrogen and oxygen come into contact with each other in the presence of a catalyst, catalytic combustion occurs by the following reaction and water is generated.

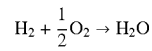

The Gibbs free energy change at 25° C. in this reaction is −237.2 kJ/mol, and this is assumed as the heat of catalytic combustion.

Shape-memory alloys and bimetals are conventionally well-known as materials, which transform with temperature. The shape-memory alloys, such as a TiNi alloy, transform into a shape preliminarily memorized at a predetermined temperature or more. The bimetals include two pieces of metal plates with different coefficients of thermal expansion. Utilizing the property of a change in the bending depending on a change in temperature, the bimetals are used for thermometers and temperature control units. Examples of bimetals using fine processing are disclosed in Japanese Patent Application Laid-Open No. 2000-246676, and an example of forming a relay is provided in H. Jerman, J. Micromech. Microeng. 4 (1994) 210-216.

The relationship between the temperature and the distortion in the cantilever structure of a bimetal material is shown as follows by S. Timoshenko, J. Opt. Soc. Am., 11 (1925) 233-255.

At first, curvature ρ and displacement y of the tip when the temperature of a bimetal including the first layer having a thickness t1 and a length l and the second layer having a thickness t2 and a length l is increased by $\Delta T$ are represented by the following expression:

$$\frac{1}{\rho} = \frac{6(\alpha_1 - \alpha_2)\Delta T(t_1 + t_2)t_1 t_2 E_1 E_2}{3(t_1 + t_2)^2 t_1 t_2 E_1 E_2 + (t_1 E_1 + t_2 E_2)(t_1^3 E_1 + t_2^3 E_2)}$$

$$y = 2\rho\sin^2\left(\frac{l}{2\rho}\right).$$

In the above expression, $E_1$ and $E_2$ are longitudinal elastic coefficients of the respective layers, and $\alpha_1$ and $\alpha_2$ are thermal expansion coefficients of the respective layers.

Here, representative material values of various materials are shown in Table 1. By adequately selecting materials of the first layer and the second layer, bimetals with which a desired distortion can be obtained when a difference in the temperature occurs.

TABLE 1

| | Young's modulus [GPa] | Poisson ratio | Linear expansion coefficient [×10$^{-6}$/K] |
|---|---|---|---|
| Stainless | 197 | 0.3 | 10-17 |
| Nickel | 199.5 | 0.31 | 13.3 |
| Silicon | 160 | 0.28 | 7.6 |
| Aluminum | 72.6 | 0.345 | 23.5 |
| Platinum | 170 | 0.38 | 8.8 |
| Gold | 78.5 | 0.27 | 14.1 |
| Copper | 129.8 | 0.34 | 17 |
| Pyrex | 63 | 0.2 | 2.8 |
| Quartz | 73 | 0.17 | 0.55 |
| Polyimide | 3 | | 45-56 |
| Polyethylene | 0.4-1.3 | 0.458 | 100-200 |

Likewise, the relationship between temperature and distortion when a bimetal material is formed not on a cantilever, but on a diaphragm, is shown in the above-mentioned H. Jerman, J. Micromech. Microeng. 4 (1994) 210-216 as follows. When the internal radius of the diaphragm (part not displaced) is assumed as b and the external radius as a:

$$y = \frac{K_y}{(1+v)} \Theta a^2.$$

In the above expression, v is the Poisson Ratio of the diaphragm and $K_y$ is a constant determined by the boundary condition.

In addition:

$$\Theta = \frac{6(\alpha_1 - \alpha_2)\Delta T(t_1 + t_2)(1 + v)}{t_2^2 K_1}$$

$$K_1 = 4 + 6\frac{t_1}{t_2} + 4\left(\frac{t_1}{t_2}\right)^2 + \frac{E_1 t_1^3(1 - v_2)}{E_2 t_2^3(1 - v_1)} + \frac{E_1 t_1(1 - v_2)}{E_2 t_2(1 - v_1)}.$$

Small fuel cells have attracted attention as an energy source to be mounted on small electric apparatuses. The reason why the fuel cell is useful as a drive source of small electric apparatuses is that the amount of energy that can be supplied per volume and per weight thereof is several times to nearly 10 times greater than that of conventional secondary lithium ion batteries. In particular, hydrogen is the most suitable fuel in order to obtain a large output from a fuel cell. However, hydrogen is a gas at normal temperature, and it is necessary to store hydrogen in a small fuel tank at a high density.

The following methods for storing hydrogen in this manner are known.

The first method is compressing and storing hydrogen as a high-pressure gas. The hydrogen density per volume is about 18 mg/cm$^3$ when the gas in the tank is compressed to 200 atm.

The second method is a method to cool hydrogen to a low temperature and store it as liquid. Liquefying hydrogen requires a large amount of energy and is also problematic, because liquid hydrogen may spontaneously vaporize and leak. However, this method enables high-density storage.

The third method is storing hydrogen using a hydrogen-storing alloy. A problem with this method is that due to a large specific gravity of the hydrogen storing alloys, hydrogen at merely 2 wt % or so can be occluded and the fuel tank is heavy. However, because the volume of the occluded hydrogen is large, this method is effective for miniaturization.

Power generation by a polymer electrolyte fuel cell is performed as follows. Perfluorosulfonic acid-based cation-exchange resin is often used for a polymer electrolyte membrane. For example, Nafion by DUPONT is well known for such a membrane.

A membrane electrode assembly, which is formed by sandwiching a polymer electrolyte membrane with a pair of porous electrodes carrying a catalyst such as platinum, that is, with a fuel electrode and an oxidizer electrode provides a power generation cell.

When an oxidizer is supplied to the oxidizer electrode while a fuel is supplied to the fuel electrode in this power generation cell, protons move in the polymer electrolyte membrane, and power is generated.

Japanese Patent Application Laid-Open No. H8-315847, for example, proposes the following safety measure in case fuel leaks from a fuel cell.

This measure includes providing a blocking unit, which blocks the supply of the fuel to the main body of the fuel cell when fuel leaks out, and linking this blocking procedure to the detection procedure by a fuel detection sensor.

As for the fuel detection unit of the fuel cell, methods for detection via a decrease in the power generation of the fuel cell, or, when the fuel is a gas, methods by mixing detection materials, such as odor-emitting materials or helium, and the like methods have been tried.

Also, solenoid valves have been used as a unit for blocking the fuel.

In small fuel cells, a method of supplying a consumed amount of fuel from a fuel tank with the outlet in a closed condition and without circulating the fuel (dead end method) is often used. However, there is a problem in that impurity gases, such as nitrogen and steam, penetrate the electrolyte film and are accumulated in the fuel channel, which causes a decrease in the power generation over time. Therefore, a scavenging (purging) procedure is often performed to drain the accumulated impurity gases in the fuel cells adopting the dead-end method. The ON/OFF change of the purging procedure was controlled by time, the output of the fuel cell, and gas concentration in the fuel channel.

However, conventional gas sensors for detecting combustible gas described above have the following problems.

For example, the adsorption-type gas sensors have very poor stability and response at the normal temperature, and a method of warming the device with a heater is used to improve the response. However, when a heater is used, electricity should be continuously applied to the exothermic body even during standby time, which causes an increase in the power consumption of the sensor. The gas heat conduction-type combustible gas sensors are not suitable for detecting combustible gas at a concentration of about several percent, because the combustible gas concentration (hereinbelow, referred to as detection limit concentration) detectable by such sensors is high. In addition, electricity should be continuously applied to the exothermic body even during standby time, which increases power consumption of the sensor. Besides, conventional adsorption-type, catalytic combustion-type, gas heat conduction-type and the like combustible gas sensors detect a change in the voltage or electrical resistance as an analog signal and, consequently, are susceptible to noise. Furthermore, miniaturization of the processing circuit of the detection signal is difficult, and many of the sensors always consume electricity.

Because conventional combustible gas detectors as described above have problems, such as insufficient miniaturization and increased power consumption, they require a system having a larger size and excess energy in the case of using fuel cells for small size electric apparatuses.

SUMMARY OF THE INVENTION

In view of the above problems to be solved, an object of the present invention is to provide a combustible gas detector with low power consumption, low noise and high-speed response, which enable miniaturization; a process for producing the combustible gas detector; and a fuel cell system equipped with a combustible gas detector.

In order to solve the above problems, the present invention provides a combustible gas detector constituted as described below, a process for producing the combustible gas detector, and a fuel cell system equipped with the combustible gas detector.

The combustible gas detector of the present invention includes: a catalyst for reaction with the combustible gas, a first displacement unit including a flexible member, which is displaced with catalytic combustion caused by the reaction of the catalyst with the combustible gas, and electrical contacts, which are switched by the displacement of the flexible member in the first displacement unit.

In the combustible gas detector of the present invention, the catalyst can include a material such as platinum.

In the combustible gas detector of the present invention, the flexible member in the first displacement unit can be one of a diaphragm and a cantilever.

In the combustible gas detector of the present invention, the diaphragm or the cantilever can include one of a laminate formed of a plurality of materials having different thermal expansion coefficients and a shape-memory alloy.

In the combustible gas detector of the present invention, the diaphragm or the cantilever can include a displacement unit, which adsorbs the combustible gas and expands with catalytic combustion caused by the reaction of the above catalyst with the combustible gas.

In the combustible gas detector of the present invention, the diaphragm can constitute a partition wall, which the combustible gas cannot penetrate and which is provided between the catalyst and the electrical contact.

In the combustible gas detector of the present invention, a heat conduction member can be provided between the first displacement unit and the catalyst.

In the combustible gas detector of the present invention, a distance between the electrical contacts is shorter than a quenching distance of the combustible gas. The shortest distance from the electrical contacts to the outer end of the flexible member is longer than the quenching distance of above combustible gas.

The combustible gas detector of the present invention can further include a second displacement unit including a flexible member, which is displaced by temperature to a direction opposite to a displacement direction of the flexible member in the first displacement unit, where the second displacement unit is provided with the first displacement unit through a heat insulating layer in-between.

The combustible gas detector of the present invention can further include a second displacement unit that does not have a catalyst, but includes a flexible member having the same displacement characteristics by temperature as the first displacement unit, wherein the second displacement unit is provided so that it can be displaced to the same direction as the displacement direction of the first displacement unit.

In addition, the combustible gas detector array of the present invention includes: a first combustible gas detector including any of the above combustible gas detectors, and a second combustible gas detector having no catalyst and including a flexible member, which is displaced by temperature, and an electrical contact switchable by the displacement of the flexible member, wherein the first combustible gas detector and the second combustible gas detector are arranged in one of a parallel state and a stacked state.

The combustible gas detector array of the present invention can include any of the above combustible gas detectors.

In the combustible gas detector array of the present invention, the flexible members in the plurality of the detectors are different in one of length, width, and thickness.

In the combustible gas detector array of the present invention, the catalysts in the plurality of the detectors are different in one of kind, amount, and disposed position.

The combustible gas detector array as mentioned herein can be taken, as a whole, as one combustible gas detector. Therefore, the combustible gas detector array is simply mentioned hereinbelow as a combustible gas detector in some cases.

The process for producing a combustion gas detector according to the present invention includes: forming a lower electrode on an electrical and heat-insulating layer formed on a substrate; forming a sacrifice layer including a supporting layer on the electrical and heat-insulating layer including the lower electrode; forming an upper electrode on the sacrifice layer including the supporting layer; forming a bimetal lower layer on the sacrifice layer including the upper electrode and then forming a bimetal upper layer on the bimetal lower layer; and forming a catalytic layer on the bimetal upper layer, then etching the sacrifice layer to release a cantilever by the bimetal upper layer and the lower layer, and forming an upper electrode on the cantilever while forming a lower electrode on the electrical and heat-insulating layer of the above substrate.

The process for producing a combustion gas detector according to the present invention includes: forming a bimetal lower layer on an electrical and heat insulating layer formed on a first substrate and then forming a bimetal upper layer on the bimetal lower layer; forming a catalytic layer on the bimetal upper layer; etching a surface side of the first substrate opposite to a side on which the catalytic layer is formed, and then forming an upper electrode layer on a remaining surface of the first substrate, which is not etched; providing a second substrate, etching the second substrate to form supporting layers on the both end sides of the second substrate, and forming a lower electrode layer in a region sandwiched between the supporting layers; and bonding the first substrate on which the above upper electrode layer is formed and the second substrate on which the above lower electrode layer is formed such that the upper electrode layer and lower electrode layer face each other.

In addition, the fuel cell system of the present invention includes any of the above combustible gas detectors or a combustible gas detector produced by any of the above processes for producing the combustible gas detector.

Further features of the present invention will become apparent from the following description of exemplary embodiments with reference to the attached drawings.

DESCRIPTION OF THE EMBODIMENTS

Next, combustible gas detectors in the form of embodiments of the present invention are described.

First Embodiment

In the first embodiment, the constitution example of the combustible gas detector using a cantilever for a flexible member is described.

Figure 1:
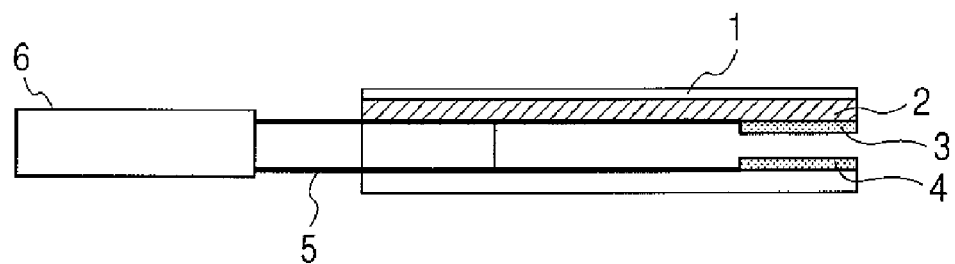
FIG. 1 is a side cross-sectional view illustrating a constitution example of the combustible gas detector using a cantilever as a flexible member in a first embodiment of the present invention.
Figure 2:
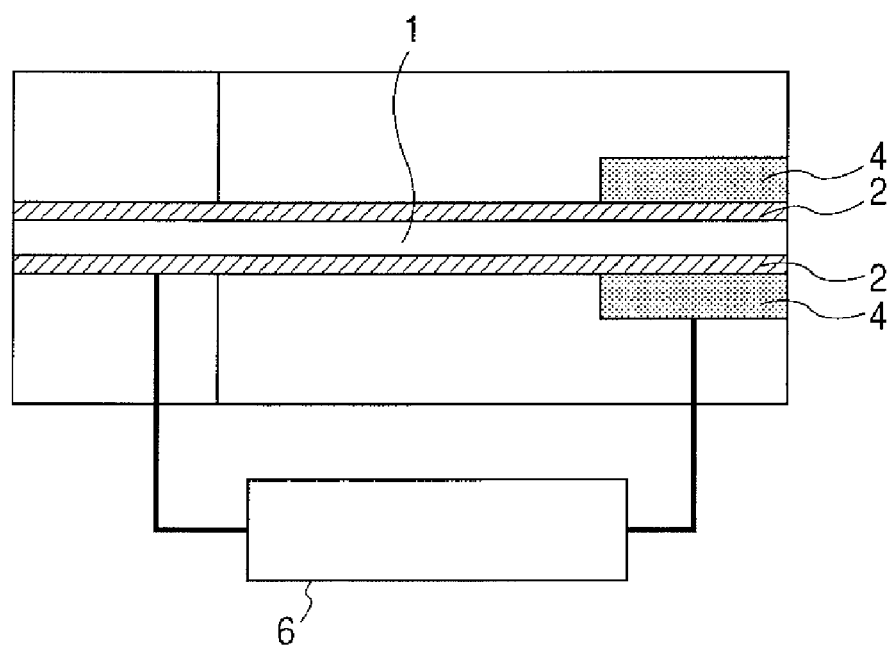
FIG. 2 is a top view illustrating a combustible gas detector in the first embodiment of the present invention.

FIG. 1 shows a side cross-sectional view illustrating the combustible gas detector in this embodiment. FIG. 2 shows the top view thereof.

The combustible gas detector according to this embodiment includes a catalytic layer 1, a cantilever 2 having a displacement layer, an upper electrode 3, a lower electrode 4, a wiring 5, and a detector 6.

Here, when hydrogen is selected as a detection gas, for example, platinum is suitable as a material constituting the catalytic layer 1. When carbon monoxide is contained in the detection atmosphere, contamination of the catalyst by carbon monoxide can be prevented by using a compound of platinum and ruthenium.

In the example illustrated by FIG. 1, the cantilever 2 consists only of a displacement layer. The cantilever does not necessarily consist only of a displacement layer and may have a flexible substrate for maintaining the structure in addition to the displacement layer. The upper electrode 3 may include a member different from the cantilever or may serve as the substrate of the cantilever or the displacement layer of the cantilever.

When a detection gas comes into contact with the catalytic layer 1, catalyzed combustion occurs via a reaction with atmospheric oxygen and heat is generated.

This heat generation causes displacement layer (cantilever) 2 to be displaced so that upper electrode 3 and lower electrode 4 come close.

When a palladium film is used as the displacement layer, for example, hydrogen becomes ready to be adsorbed by heat generation and such a displacement is caused as the film expands. In addition, for example, shape-memory alloys, such as TiNi alloys, can be used as the displacement layer by which the shape can be memorized so that displacement occurs at or at higher than a predetermined temperature. Furthermore, for example, distortion with increased temperature can be caused by using a bimetal as the displacement layer in which two kinds of films having different temperature expansion coefficients are laminated. When a bimetal is used for the displacement layer, one of the two kinds of films constituting the bimetal may serve as the catalytic layer 1.

Figure 9:
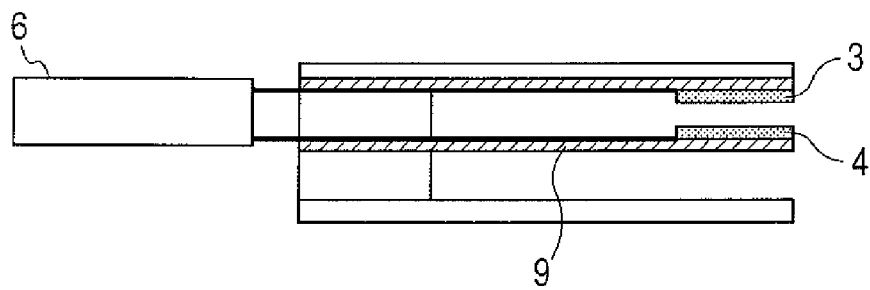
FIG. 9 is a side cross-sectional view illustrating a second constitution example in the first embodiment of the present invention in which changes in the external environment temperature are corrected.
Figure 11:
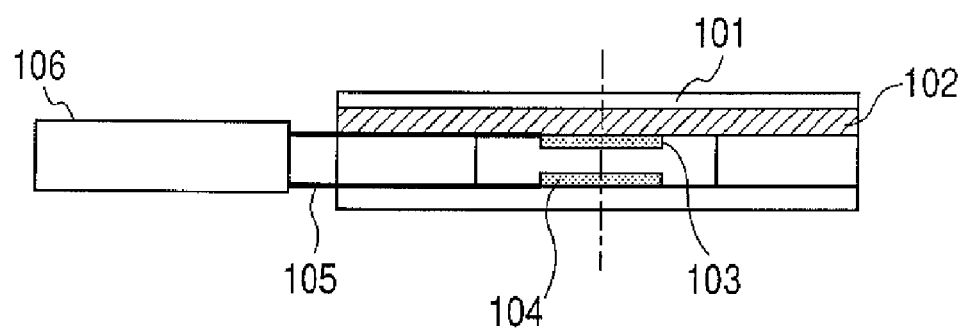
FIG. 11 is a side cross-sectional view illustrating the constitution example of the combustible gas detector using a diaphragm as a flexible member in a second embodiment of the present invention.

When the cantilever is distorted upon heat generation to not less than a certain degree, the upper electrode 3 incorporated with the cantilever 2 and the facing lower electrode 4 are in contact, and an electric signal is transferred to the detector 6. This allows the recognition that the hydrogen concentration exceeds a certain value (detection limit concentration). When the hydrogen concentration is again under the detection limit concentration, heat generation in the catalyst part is controlled, the cantilever is restored and the electrodes get separated. When the distance between two facing electrodes (electrical contacts) is made smaller than the quenching distance of the combustible gas or the distance from the electrode to the cantilever external edge is set larger than the quenching distance of the combustible gas, a possibility of the firing upon the contact of the contacts is eliminated to enhance safety. For example, the quenching distance is 0.6 mm in the case of the hydrogen combustible gas. Here, the distance between two electrical contacts strictly means a distance between two members each having an electrical contact. For example, in FIG. 1, the above distance is a distance between the substrate portion having the lower electrode 4 and the cantilever 2. In FIG. 9, the above distance is a distance between the first cantilever 2 and the second cantilever 9. FIG. 11, the above distance is a distance between the substrate portion having the lower electrode 104 and the diaphragm 102.

Some other variations of the present embodiment are shown as follows.

The combustible gas detector mentioned above is one in which the upper electrode 3 and the lower electrode 4 are in contact when the gas concentration exceeds a predetermined gas concentration, thereby turning ON the electrical contacts. In contrast, another construction in which the above electrical contacts turn OFF over a predetermined temperature can be made, as show it in FIGS. 3 and 4.

Figure 3:
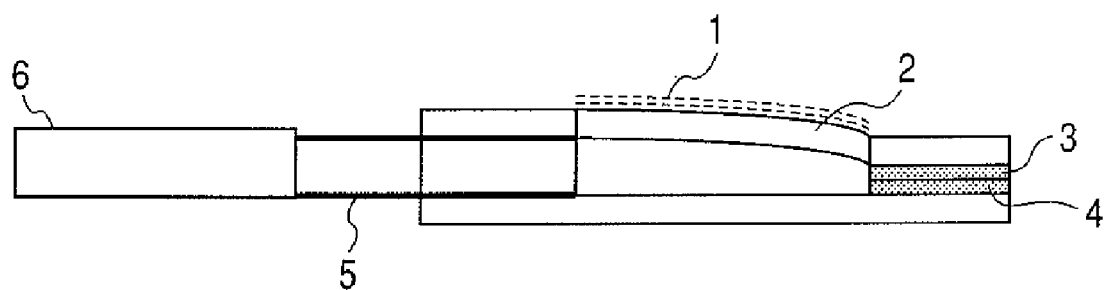
FIG. 3 is a side cross-sectional view illustrating a constitution example in the first embodiment of the present invention in which the cantilever is deformed beforehand to contact the electrode so that the electrical contact turns OFF at a predetermined temperature or higher.
Figure 4:
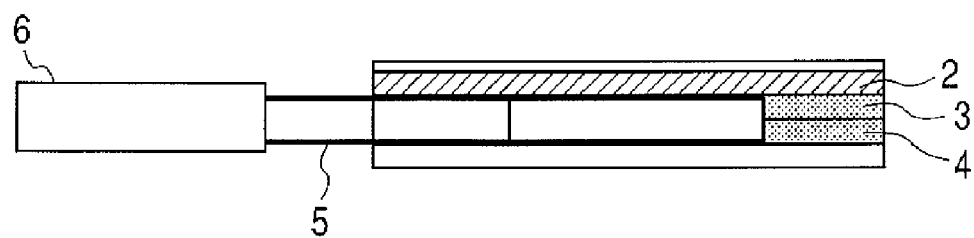
FIG. 4 is a side cross-sectional view illustrating a constitution example in the first embodiment of the present invention in which the gap between the electrode pads is eliminated beforehand so that the electrical contact turns OFF at a predetermined temperature or higher.

Side cross-sectional views illustrating the above constitution example of the combustible gas detector of the applied form are shown in FIGS. 3 and 4.

FIG. 3 illustrates a constitution example in which the cantilever 2 is deformed beforehand using an internal stress or the like so that the upper electrode 3 and the lower electrode 4 are contacted and the upper electrode and the lower electrode separate (that is, the electrical contact turns OFF) at or at higher than a predetermined temperature. FIG. 4 illustrates a constitution example in which the upper electrode 3 and the lower electrode 4 are provided so that the gap between the electrodes is eliminated beforehand, and the cantilever 2 is designed to deflect upward in the drawing. Thereby, the electrical contact turns OFF at or at higher than a predetermined temperature. In either case of FIG. 3 or 4, the displacement layer is displaced to the direction with the increase in temperature so that opposite electrodes will be separated.

Figure 5:
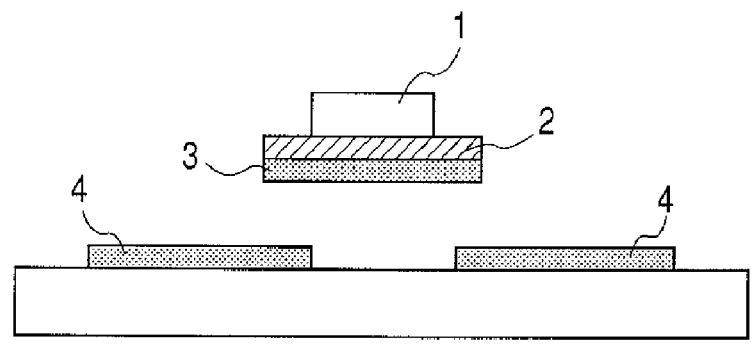
FIG. 5 is a diagram illustrating a constitution example in the first embodiment of the present invention in which the upper electrode on the cantilever is connected to two lower electrodes on the substrate.

The electrode layer can be constituted as shown in FIG. 5.

In this case, the upper electrode 3 on the cantilever is displaced so as to connect two lower electrodes 4 on the substrate. Such disposition of the electrodes eliminates the need to put a wiring on the cantilever, except on the upper electrode, and can simplify the production process.

Figure 6:
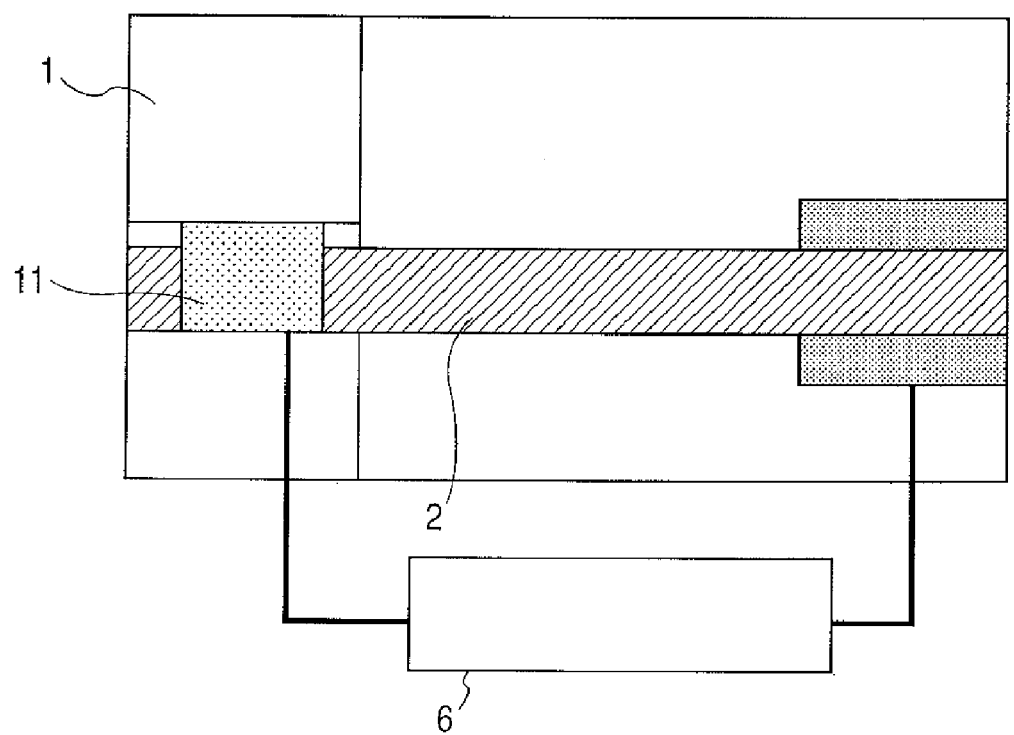
FIG. 6 is a top view illustrating a constitution example in the first embodiment of the present invention in which the catalyst portion and the cantilever are disposed away from each other.

The catalytic layer 1 and the cantilever 2 can be disposed separately, as shown in the top view of FIG. 6. In this case, the catalytic layer and the displacement layer in the cantilever can be connected with a member 11 having a higher heat conductance.

In addition, a plural number of the above combustible gas detectors can be disposed (as a combustible gas detector array) and used.

This improves reliability of the sensor and allows the determination of the spatial distribution of the concentration.

Figure 7:
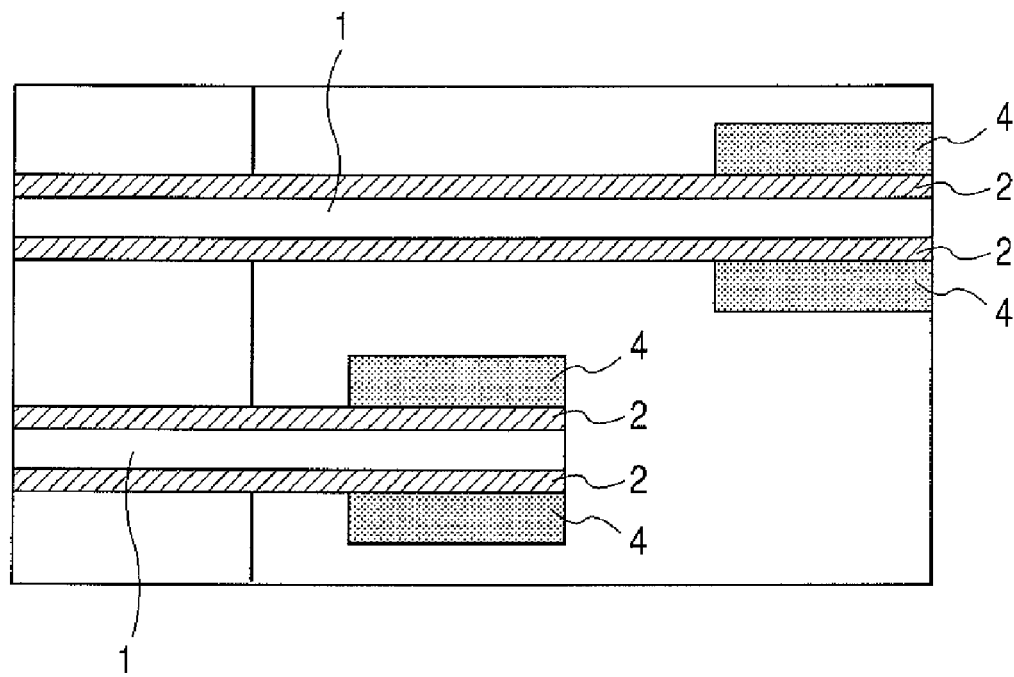
FIG. 7 is a diagram illustrating a constitution example in the first embodiment of the present invention in which a plurality of cantilevers having different lengths are provided so that detection limit concentration may be different for every cantilever.

Also, a plurality of cantilevers having different lengths may be provided so that the detection limit concentration may be different for every cantilever as shown in FIG. 7. The range of combustible gas concentration can be determined in more detail by constituting the device in this way.

The constitution examples so as to make the detection limit concentration different for every cantilever include, in addition to the constitution to vary the length of the cantilevers, constitutions to vary the width, thickness, or material of the cantilever, constitutions to vary the kind or the amount of the catalyst, and constitutions to vary the position of the catalyst.

In the combustible gas detectors as described above, displacement of the cantilever may be caused by changes in the environmental temperature. In that case, changes in the external environment temperature can be corrected by the constitution as shown below.

Figure 8:
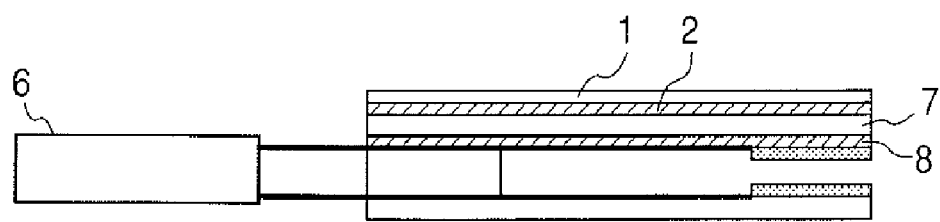
FIG. 8 is a side cross-sectional view illustrating a first constitution example in the first embodiment of the present invention in which changes in the external environment temperature are corrected.

A side cross-sectional view illustrating a first constitution example in which changes in the external environment temperature are corrected is shown in FIG. 8.

The first constitution example disposes the second displacement layer 8 and the catalytic layer 1 with the heat insulating barrier 7 between them as shown in FIG. 8. This second displacement layer 8 is made so as to be displaced to the direction opposite to the first displacement layer on this occasion. This constitution cancels the forces to deform the first displacement layer and the second displacement layer and prevents displacement from occurring when the external environment temperature changes without catalyzed combustion. Only the first displacement layer is displaced when catalyzed combustion occurs. This is because the heat of the catalyzed combustion is not transmitted to the second displacement layer 8 due to the heat insulating layer 7.

Next, another side cross-sectional view illustrating a second constitution example in which changes in the external environment temperature are corrected is shown in FIG. 9.

The second constitution example is constituted so that a second cantilever 9 is provided as shown in FIG. 9. This second cantilever 9 does not have a catalytic layer, and the displacement characteristics thereof by the temperature are almost equivalent to the first cantilever 2.

When the environmental temperature changes, the first cantilever 2 and the second cantilever 9 are displaced in the same way, and the gap between them does not change.

At the time of catalyzed combustion, only first cantilever 2 is displaced, and electrode pads provided on each of the first and the second cantilevers contact each other. Thereby, the contact turns ON.

Figure 10:
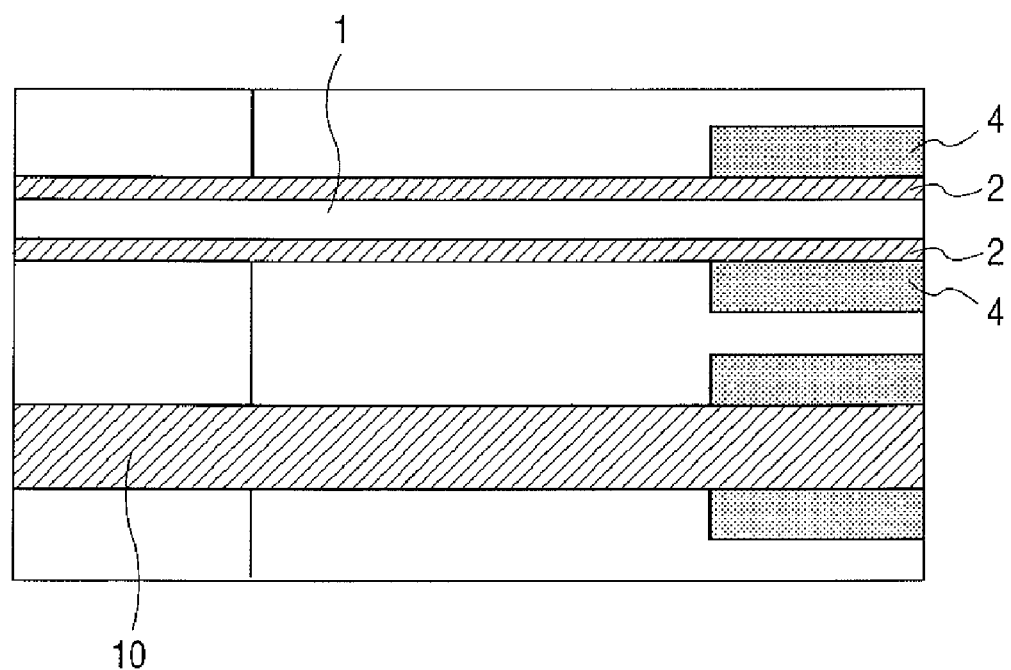
FIG. 10 is a side cross-sectional view illustrating a third constitution example in the first embodiment of the present invention in which changes in the external environment temperature are corrected.

Next, another side cross-sectional view illustrating a third constitution example in which changes of the external environment temperature are corrected is shown in FIG. 10.

The third constitution example constituted so that the second detector 10 is provided as shown in FIG. 10.

This second detector 10 does not have a catalytic layer, and the displacement characteristics thereof by the temperature are almost equivalent to the first detector.

When the environmental temperature changes, the first detector and the second cantilever 10 are displaced in the same way. Therefore, when both are turned ON, it is not caused by detection of a gas, but by a change in the environmental temperature.

At the time of catalyzed combustion, only the first detector turns ON. By the difference in this signal, temperature compensation can be performed.

Second Embodiment

As the second embodiment, the constitution example of the combustible gas detector using a diaphragm for a flexible member is described.

Figure 12:
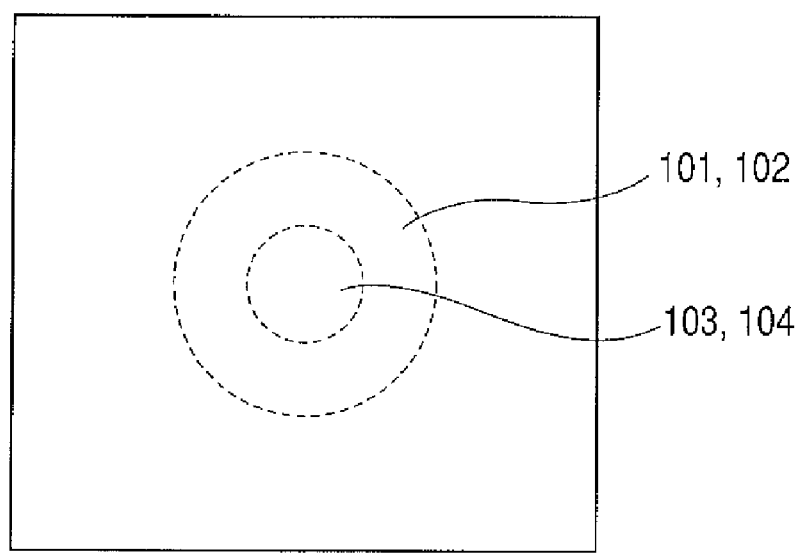
FIG. 12 is a top view illustrating a constitution example of the combustible gas detector using a diaphragm as a flexible member in the form of the second embodiment of the present invention.

FIG. 11 shows a side cross-sectional view illustrating the combustible gas detector in this embodiment. FIG. 12 shows the top view thereof.

The combustible gas detector according to this embodiment includes a catalytic layer 101, a displacement layer (diaphragm) 102, an upper electrode 103 constituting a pair of electrode pads, a lower electrode 104, a wiring 105, and a detector 106.

Here, when hydrogen is selected as a detection gas, for example, platinum is suitable as a material constituting the catalytic layer 101. When carbon monoxide is contained in the detection atmosphere, catalyst poisoning by carbon monoxide can be prevented by using a compound of platinum and ruthenium.

When a detection gas contacts the catalytic layer 101, catalyzed combustion occurs by a reaction with atmospheric oxygen and heat is generated.

This heat generation causes displacement layer (diaphragm) 102 to be displaced so that opposite electrodes come close.

A displacing mechanism in which a palladium film is the displacement layer, for example, and in which hydrogen becomes ready to be adsorbed by heat generation and the film expansion can be used.

As an alternative, shape-memory alloys, such as TiNi alloys, can be used as the displacement layer, so that the shape can be memorized and the displacement can occur at or at higher than a predetermined temperature.

As another method, distortion with increased temperature can be caused by using a bimetal as the displacement layer in which two kinds of films having different temperature expansion coefficients are laminated.

At this time, one of the two kinds of films constituting the bimetal may serve as the catalytic layer 101.

The diaphragm 102 may include only the above displaced material or may have a substrate to maintain the structure.

When the diaphragm is distorted upon heat generation to not less than a certain degree, the upper electrode 103 and the facing lower electrode 104 come into contact and an electricity signal is transferred to the detector 106. This allows to recognize that the hydrogen concentration exceeds a certain value.

The electrode pads on the diaphragm may include a member for this purpose or may also serve as a substrate of the diaphragm or the displacement layer.

When the hydrogen concentration is again under the detection limit concentration, heat generation in the catalyst part is controlled, the diaphragm is restored, and the electrodes get separated.

The manner of turning ON in a normal state, examples of disposition of the electrode pads, use of a plurality of detectors, and temperature compensation are similar to those in the First Embodiment.

When a diaphragm is used rather than a cantilever, displacement is hard to achieve. However, safety can be improved, because the catalytic layer and electrode pads are separated by the diaphragm.

According to the combustible gas detectors of the abovementioned First and Second Embodiments, electric power is substantially not consumed during the standby time and detection is performed by the judgment of the ON/OFF state of the contacts. Accordingly, the mechanism is simple, the device easy to miniaturize, and robustness to noise can be realized.

In addition, a mechanism of the detect circuit can be simplified and structured so that it is easy to miniaturize.

Also, detection accuracy can be improved by integrating a plurality of sensors, which switch at different concentrations.

In particular, for fuel cells, they can be used for leak detection and as purging (scavenging) control units.

The combustible gas detectors of the present invention can be configured as detectors, which are more readily switched as the external environment temperature is elevated, enabling fuel cells to be more safely operated.

Working examples of the present invention are described below.

EXAMPLE 1

Example 1 is a constitution example of the combustible gas detector, which uses a bimetal cantilever as a flexible member.

The combustible gas detector of this Example can be produced by a conventional machining technique, but, here, the production process using a semiconductor processing technique is described. Size and materials of each part may be variously combined. One example of those is shown here.

Figure 13:
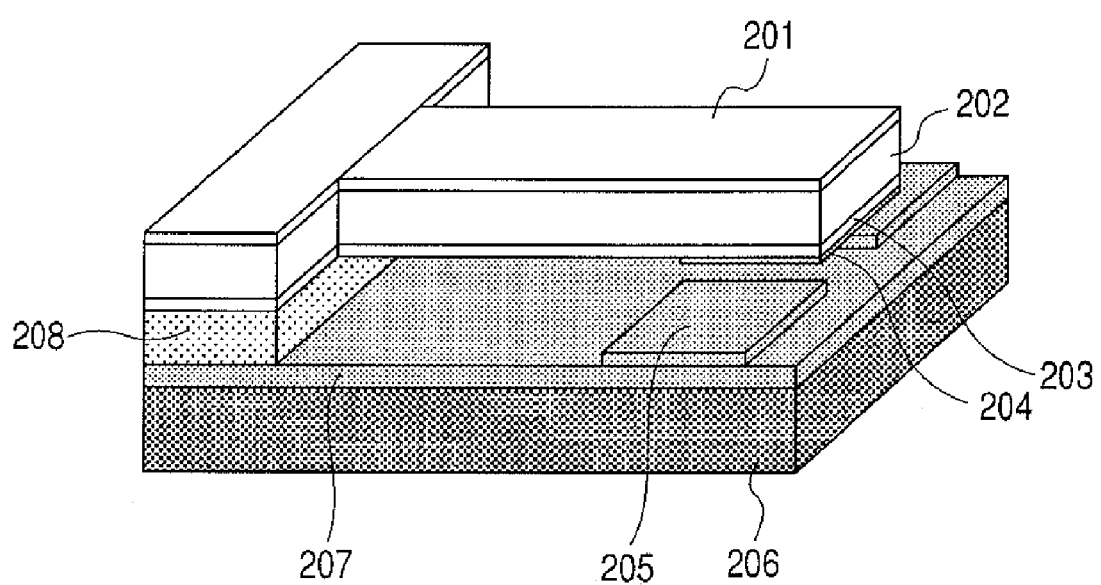
FIG. 13 is a perspective view illustrating a constitution example of the combustible gas detector in Example 1 of the present invention.

A perspective view illustrating the constitution example of the combustible gas detector of this Example is shown in FIG. 13.

The combustible gas detector of this Example has an oxide layer 207 for electrical insulation and heat insulation and a lower electrode 205 on a silicon substrate 206.

A cantilever is provided on a supporting layer 208 made of nickel.

The cantilever has an aluminum layer and a platinum layer on a silicon beam, and a bimetal lower layer 203 made of silicon and a bimetal upper layer 202 made of aluminum form a bimetal. Platinum forms a catalytic layer 201. The upper electrode 204 is formed on the tip of the cantilever.

The dimensions of respective parts are as follows.

The thickness of an insulating layer 207 is 0.5 μm, the thickness of a supporting layer 208 is 5 μm, and the size of the electrodes 204 and 205 are 500 μm×500 μm×0.5 μm.

The cantilever has a length of 1,000 μm and width of 500 μm. The thickness of the silicon layer is 5 μm, the thickness of the aluminum layer is 5 μm, and the thickness of the platinum layer is 1 μm.

Next, the process for producing the combustible gas detector in this Example by the semiconductor processing technique is described.

FIGS. 14A to 14E and 15A to 15C are side sectional views illustrating respective production steps of the production procedure of this Example.

Figure 14A:
FIGS. 14A, 14B, 14C, 14D, and 14E are side cross-sectional views illustrating the production steps of a process for producing the combustible gas detector in Example 1 of the present invention.

The first step shown in FIG. 14A is a step of forming an electrical and heat insulating layer 207 on the surface of silicon substrate 206.

As the silicon substrate 206, a 525 μm thick substrate, one side of which is polished, can be used. An electrical and heat insulating layer 207 having a thickness of around 0.5 μm can be formed on the surface of a silicon substrate by heat oxidation.

Figure 14B:
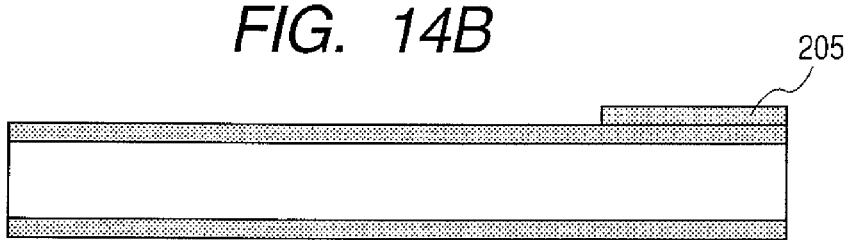

Next, the second step shown in FIG. 14B is a step of forming a lower electrode 205 and a wiring.

Au, which has corrosion resistance and low electrical resistance, is suitable for the electrode.

As for the formation of the electrode, a photoresist mask is formed by photolithography at first and a thin film of Cr or Ti is formed to enhance the close contact of the film and, further on that, Au is deposited in a thickness of 0.5 µm.

Sputtering and ion beam vapor deposition are suitable for the film formation.

After film formation, the mask that serves as a sacrifice layer is removed with a solvent to pattern the electrodes and wirings (so-called liftoff method).

Figure 14C:
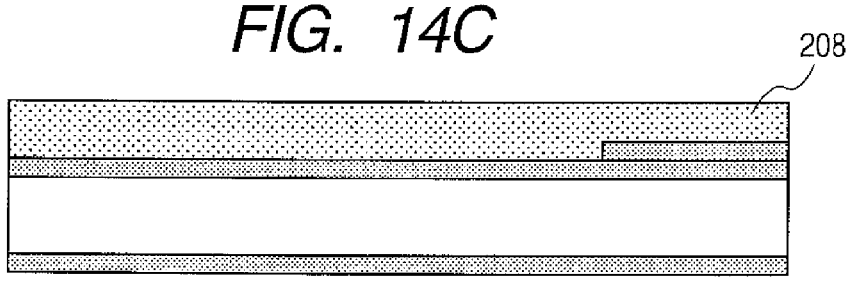

Next, the third step as shown in FIG. 14C is a step of forming the supporting layer and the sacrifice layer 208 of the cantilever.

Ni is vapor-deposited to 5 µm. When the film is thick, it is effective to form the film by plating.

Figure 14D:
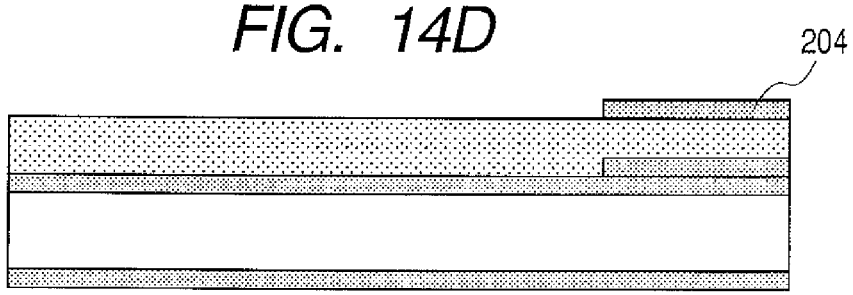

Next, the fourth step as shown in FIG. 14D is a step of forming upper electrode 204.

Likewise, the lower electrode, Au, which has corrosion resistance and low electrical resistance, is suitable for the electrode.

As for the formation of the electrode, a photoresist mask is formed by photolithography at first and a thin film of Cr or Ti is formed to enhance the close contact of the film and, further on that, Au is deposited in a thickness of 0.5 µm.

Sputtering and ion beam vapor deposition are suitable for film formation.

After film formation, the mask that serves as the sacrifice layer 208 is removed with a solvent to pattern the electrodes and wiring.

Figure 14E:
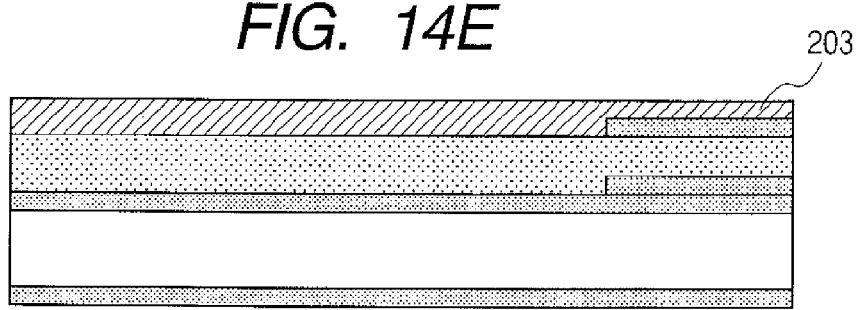

Next, the fifth step as shown in FIG. 14E is a step of forming bimetal lower layer 203. Silicon is deposited in a thickness of 5 µm and patterned. Sputtering and the like are usable for the film formation of silicon.

For patterning, a shadow mask can be used at the time of film formation, and dry etching or wet etching can be used after film formation.

Figure 15A:
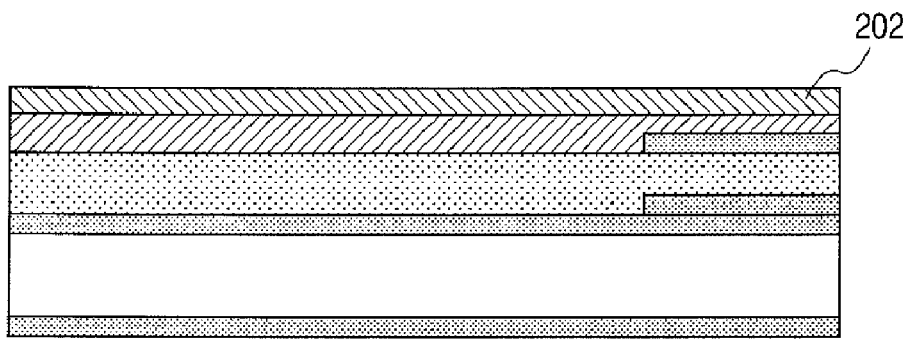
FIGS. 15A, 15B, and 15C are side cross-sectional views illustrating the production steps of a process for producing the combustible gas detector in Example 1 of the present invention, which follows the steps illustrated in FIGS. 14A to 14E.

Next, the sixth step as shown in FIG. 15A is a step of forming bimetal upper layer 202.

Al is deposited in a thickness of 5 µm and patterned. Sputtering and vacuum deposition are usable for the film formation.

For patterning, a shadow mask can be used at the time of film formation, and wet etching can be used after film formation.

Although various kinds of acids and alkali can be used for etching, conventional mixtures of phosphoric acid, nitric acid, and acetic acid can also be used.

Figure 15B:
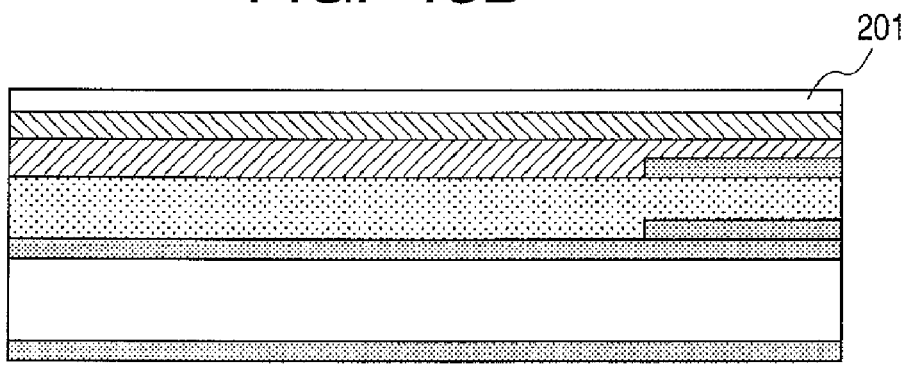

Next, the seventh step as shown in FIG. 15B is a step of forming a catalytic layer.

A photoresist mask is formed by photolithography at first and a thin film of Cr or Ti is formed to enhance the close contact of the film and, further on that, Pt is deposited in a thickness of 0.5 µm. Sputtering and plating are suitable for film formation.

After film formation, the mask, which serves as a sacrifice layer, is removed with a solvent to pattern the electrodes and the wiring. The larger is the surface area of the catalytic layer, the more readily the catalytic layer reacts with a combustible gas.

Therefore, the catalytic layer can be formed by preparing a catalyst slurry including platinum fine particles and a binder and then applying the slurry with a spray or a coater.

Figure 15C:
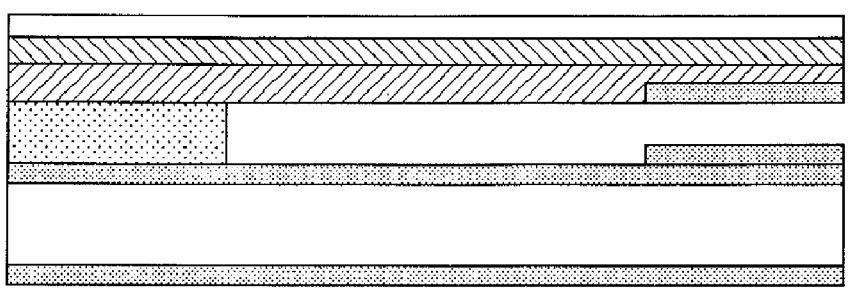

Next, the eighth step as shown in FIG. 15C is a step of releasing a cantilever.

A cantilever is released when Ni, which is a sacrifice layer, is dissolved. Several through-holes may be provided on the cantilever at this time in order to make it easy to facilitate etching of the sacrifice layer under the cantilever.

It is necessary to select an etchant so that the upper Al layer is not etched.

For example, diluted nitric acid or diluted phosphoric acid can be used.

As above, the combustible gas detector of this Example is completed.

Figure 16:
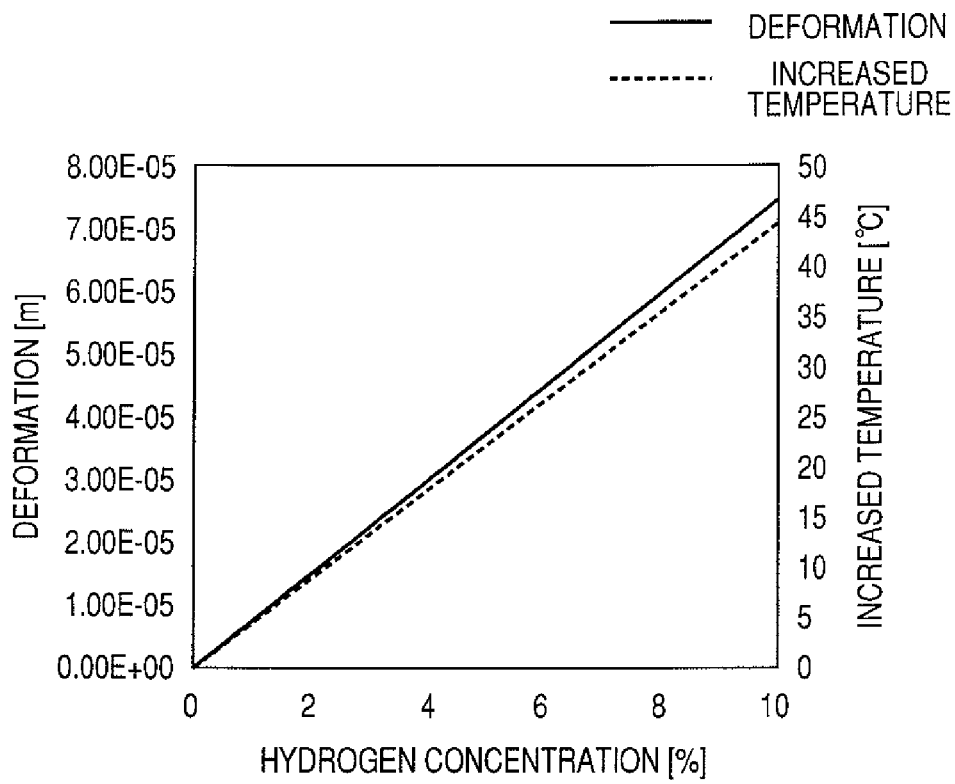
FIG. 16 is a graph of the characteristics illustrating the relationship between hydrogen concentration and the increased temperature in the catalytic combustion under a natural diffusion atmosphere and deformation of the cantilever at that time in the combustible gas detector of Example 1 of the present invention.

FIG. 16 is a graph of characteristics illustrating the relationship between hydrogen concentration and the increased temperature in the catalyzed combustion in a natural diffusion atmosphere and deformation of the cantilever at that time in the combustible gas detector of the Example of the present invention.

It can be appreciated that in the case of hydrogen, the temperature may increase by 10° C. or more even at the concentration below the explosion limit by catalyzed combustion.

The displacement of the cantilever of the case is around 10 µm, which is sufficient to cause the ON/OFF switching at the contact.

Figure 17:
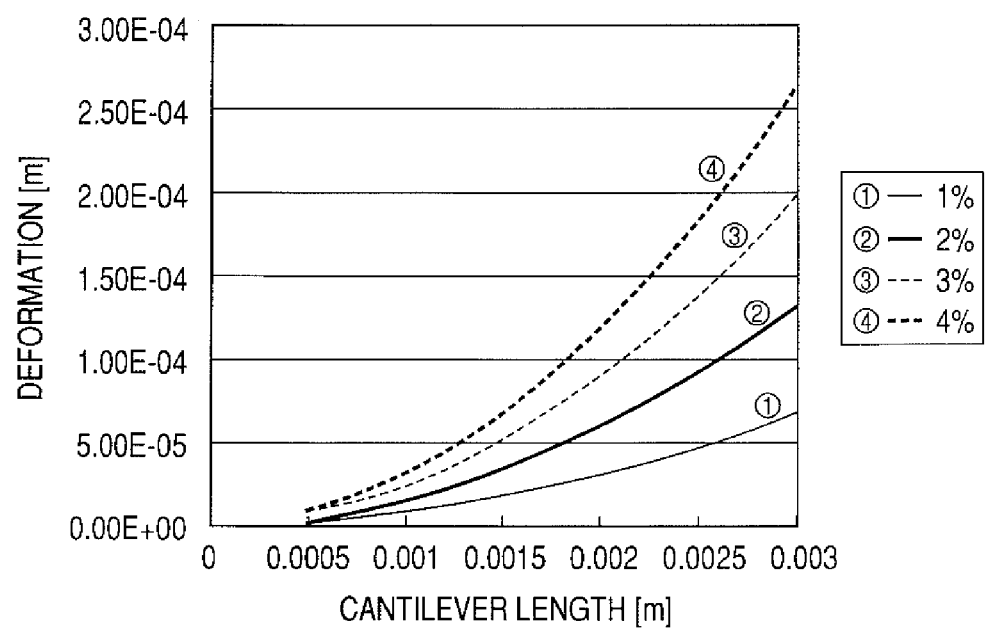
FIG. 17 is a graph of the characteristics when the length of the cantilever in the combustible gas detector of Example 1 of the present invention is varied.

FIG. 17 illustrates the displacement of the cantilever for a different concentration when only the length of the cantilever is varied without changing the kind or the thickness of the film.

It can be appreciated that the longer is the cantilever, the larger is the deformation. Therefore, detectors that can cause switching at different concentrations can be produced by changing the length of the cantilever.

For example, if the detectors with cantilevers having the lengths of 1 mm, 2 mm, 3 mm, and 4 mm are disposed, a change in the concentration can be recognized at four steps.

EXAMPLE 2

Example 2 is a constitution example of the combustible gas detector, which uses a diaphragm as a flexible member.

The combustible gas detector of this Example can be also produced by a conventional machining technique as mentioned in Example 1, but here, the production process using a semiconductor processing technique is described. Size and materials of each part may be variously combined. One example of those is shown here.

Figure 18:
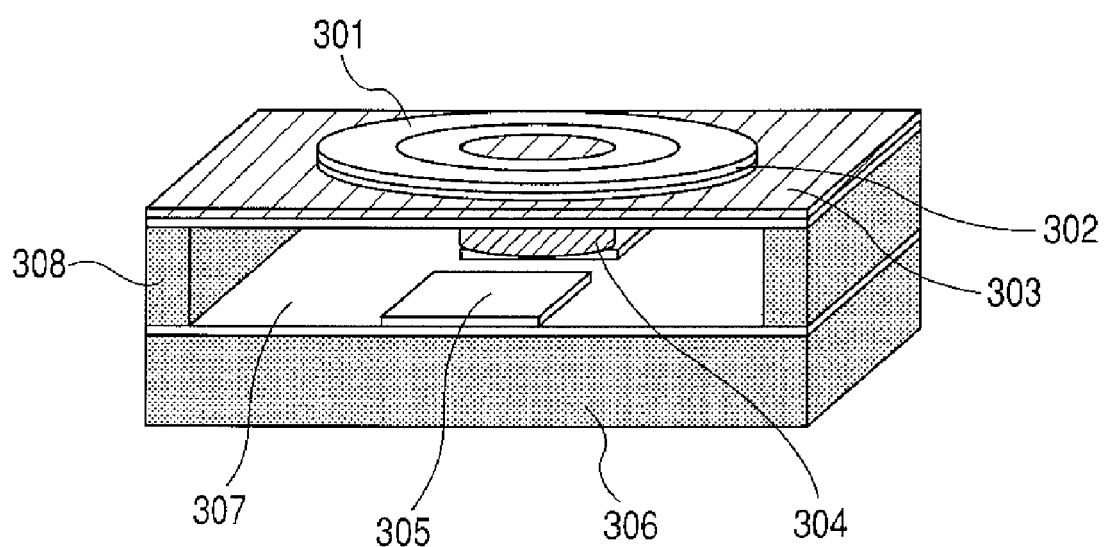
FIG. 18 is a perspective view illustrating a constitution example of the combustible gas detector in Example 2 of the present invention.

A perspective view illustrating the constitution example of the combustible gas detector of this Example is shown in FIG. 18.

The combustible gas detector of this Example has an oxide layer 307 for electrical insulation and heat insulation and a lower electrode 305 on a silicon substrate 206. A diaphragm is provided on a supporting layer 308 made of silicon.

The diaphragm has a silicon layer, an aluminum layer and a platinum layer on a silicon oxide layer, and a bimetal lower layer 303 made of silicon and a bimetal upper layer 302 made of aluminum form a bimetal. Platinum forms a catalytic layer 301.

The upper electrode 304 is formed in the center of the diaphragm.

The dimensions of respective parts are as follows.

The thickness of an insulating layer 307 is 0.5 µm, the thickness of a supporting layer 308 is 3 µm, and the size of the electrodes 304 and 305 are 500 µm×500 µm×0.5 µm.

The diaphragm has an external diameter of 2.5 mm and an internal diameter of 1.25 mm, and the thickness of the silicon layer is 5 µm, the thickness of the aluminum layer is 5 µm, and the thickness of the platinum layer is 1 µm. The internal diameter of the aluminum layer is 3.75 mm.

Next, the process for producing the combustible gas detector in this Example by the semiconductor processing technique is described.

FIGS. 19A to 19E and 20A to 20D are side sectional views illustrating respective production steps of the production procedure of this Example.

During production, two pieces of silicon substrates (wafers) are separately processed and the pieces are then bonded together.

At least one piece (diaphragm side) of the silicon substrate can be polished on both sides.

While normal silicon substrates can be used, SOI (silicon on insulator) wafers are preferred, because they enable control over the etching depth. The oxide layer can also be used as a heat insulation layer.

Figure 19A:
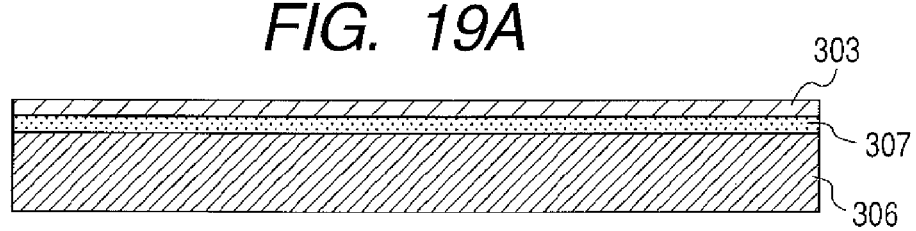
FIGS. 19A, 19B, 19C, 19D, and 19E are side cross-sectional views illustrating the production steps of a process for producing the combustible gas detector in Example 2 of the present invention.
Figure 19B:
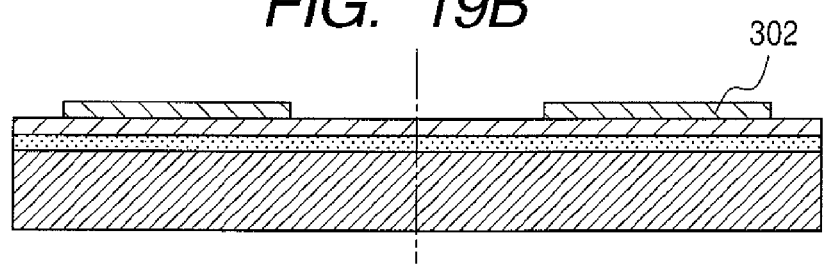

The first and second steps shown in FIGS. 19A and 19B are steps of forming a bimetal lower layer 303 made of silicon and a bimetal upper layer 302 made of aluminum on the surface of the first substrate 306 and then performing patterning.

As this substrate, a both-side polished SOI wafer having a 200 μm-thick device layer, 0.5 μm-thick BOX layer, and 5 μm-thick Si layer can be used, for example.

Al is deposited in a thickness of 5 μm and patterned. Sputtering and vacuum deposition are usable for film formation.

After film formation, a photoresist mask is formed by photolithography and, after wet etching, the resist is removed.

Figure 19C:
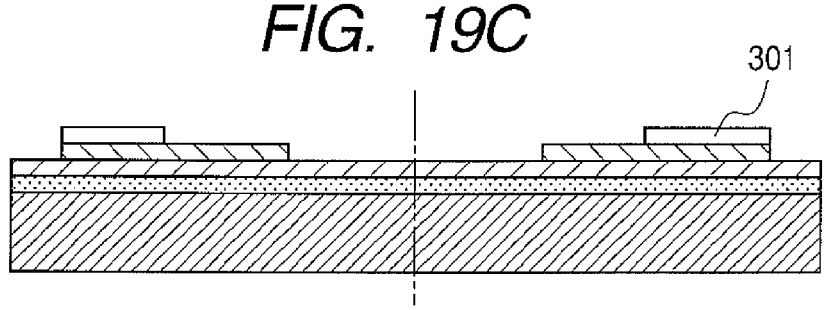

Next, the third step as shown in FIG. 19C is a step of forming a catalytic layer 301.

A photoresist mask is formed by photolithography at first, a thin film of Cr or Ti is formed to enhance the close contact of the film, and, further on that, Pt is deposited in a thickness of 0.5 μm. Sputtering and plating are suitable for film formation.

After film formation, the mask, which serves as a sacrifice layer, is removed with a solvent to pattern the electrodes and the wiring (so-called liftoff method). The larger is the surface area of the catalytic layer, the more readily the catalytic layer reacts with a combustible gas.

Therefore, the catalytic layer can be formed by preparing a catalyst slurry including platinum fine particles and a binder and then applying the slurry with a sprayer or a coater.

Figure 19D:
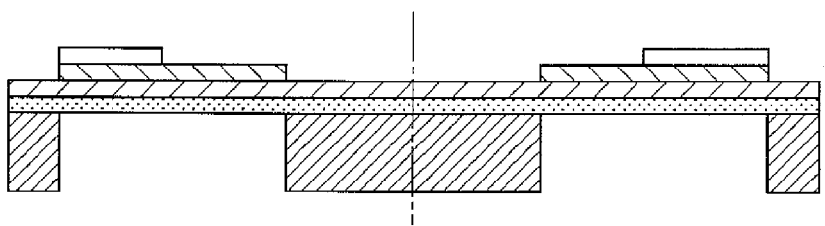

Next, the fourth step as shown in FIG. 19D is a step of etching the back of the first substrate 306. ICP-RIE (reactive ion etching) and anisotropic wet etching by KOH or TMAHI can be used for etching.

At first, the pattern of the top surface is protected with a photoresist and the back thereof is subjected to mask patterning. Then, etching is performed and the mask is removed.

At this time, if an SOI wafer is used, the oxide layer of the wafer plays a role as an etch-stop layer and thickness-controlled etching can be performed.

Figure 19E:
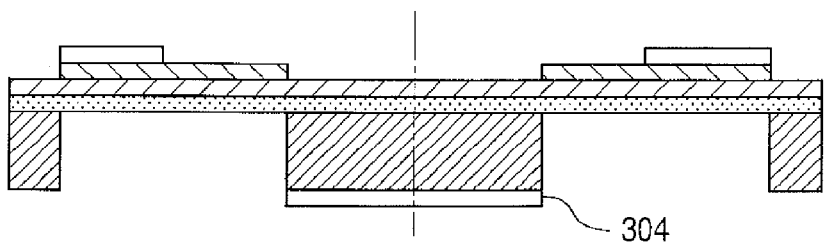

The fifth step as shown in FIG. 19E is a step of forming upper electrode 304.

Likewise the lower electrode, Au, which has corrosion resistance and low resistance, is suitable for the electrode.

As for the formation of the electrode, a photoresist mask is formed by photolithography at first, a thin film of Cr or Ti is formed thereon to enhance the close contact of the film, and, further on that, Au is deposited in a thickness of 0.5 μm.

Sputtering and ion beam vapor deposition are suitable for film formation.

After film formation, the mask, which serves as a sacrifice layer, is removed with a solvent to achieve patterning of the electrodes and wiring. A film of Au may be formed on the entire surface of the back side without performing patterning.

Figure 20A:
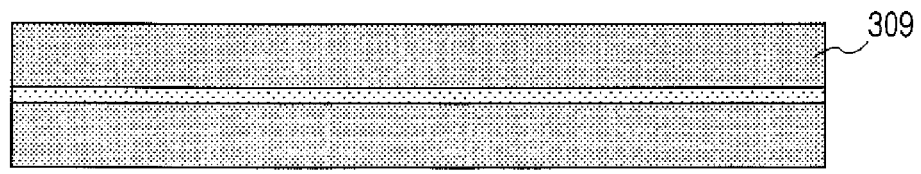
FIGS. 20A, 20B, 20C, and 20D are side cross-sectional views illustrating the production steps of a process for producing the combustible gas detector in Example 2 of the present invention, which follows the steps illustrated in FIGS. 19A, 19B, 19C, 19D, and 19E.

The second substrate is used in the sixth step shown in FIG. 20A.

Figure 20B:
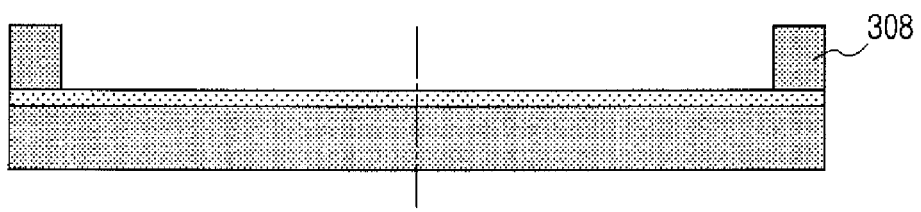

A one-side polished SOI wafer is used as this substrate. With respect to the thicknesses of respective layers, a wafer having a 200 μm device layer, a 0.5 μm BOX layer and a 3 μm Si layer can be used, for example. The seventh step as shown in FIG. 20B is a step of forming supporting layer 308. ICP-RIE (reactive ion etching) and anisotropic wet etching by KOH or TMAHI can be used for etching.

First, a mask layer is formed and patterning is performed. Then, etching is performed and the mask is removed.

At this time, if an SOI wafer is used, the oxide layer of the wafer plays a role as an etch-stop layer and thickness controlled etching can be performed.

Figure 20C:
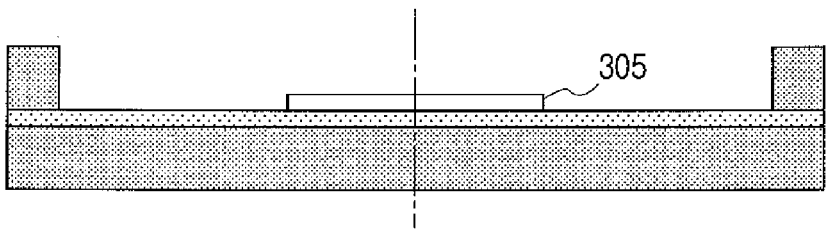

The eighth step as shown in FIG. 20C is a step of forming lower electrode 305.

Likewise, the upper electrode, Au, which has corrosion resistance and low electrical resistance, is suitable for the electrode.

As for the formation of the electrode, a photoresist mask is formed by photolithography at first, a thin film of Cr or Ti is formed thereon to enhance the close contact of the film, and, further on that, Au is deposited in a thickness of 0.5 μm.

Sputtering and ion beam vapor deposition are suitable for film formation.

After film formation, the mask, which serves as a sacrifice layer, is removed with a solvent to pattern the electrodes and wiring.

Figure 20D:
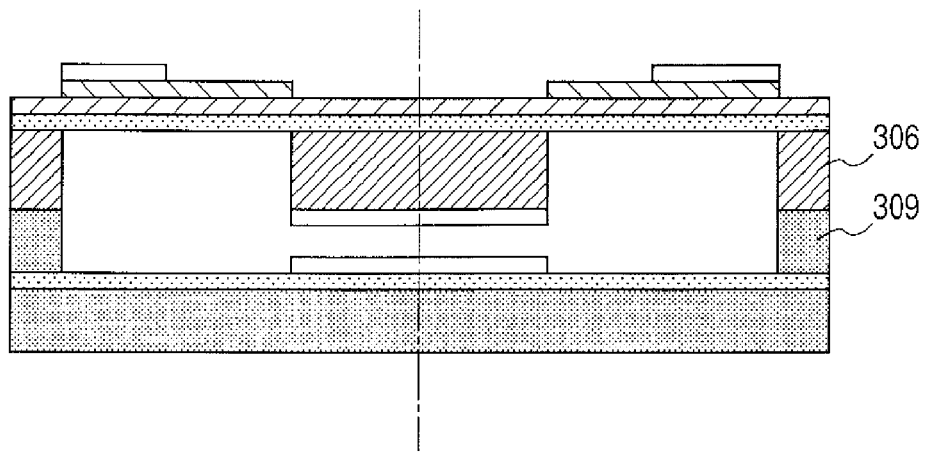

Next, the ninth step as shown in FIG. 20D is a step of laminating the first substrate and the second substrate.

The lamination may be performed by diffusion bonding or with an adhesive.

As above, the combustible gas detector of this Example is completed.

Figure 21:
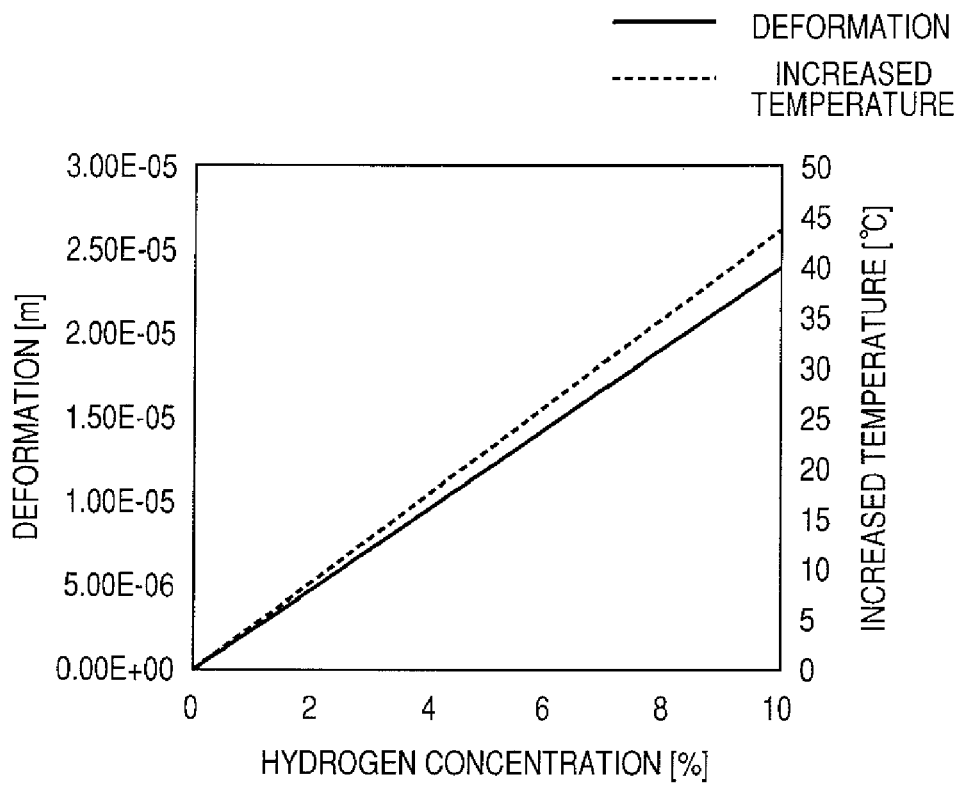
FIG. 21 is a graph of the characteristics illustrating the relationship between hydrogen concentration and the increased temperature in the catalytic combustion and deformation of the diaphragm at that time under a natural diffusion atmosphere in the combustible gas detector of Example 2 of the present invention.

FIG. 21 is a graph of characteristics illustrating the relationship between hydrogen concentration and the increased temperature in the catalyzed combustion in a natural diffusion atmosphere and deformation of the diaphragm at that time in the combustible gas detector of this Example.

It can be appreciated that in the case of hydrogen, the temperature may increase by 10° C. or more even at the concentration below the explosion limit by catalyzed combustion. The displacement of the diaphragm of the case is around 5 μm, which is sufficient to cause ON/OFF switching at the contact.

Figure 22:
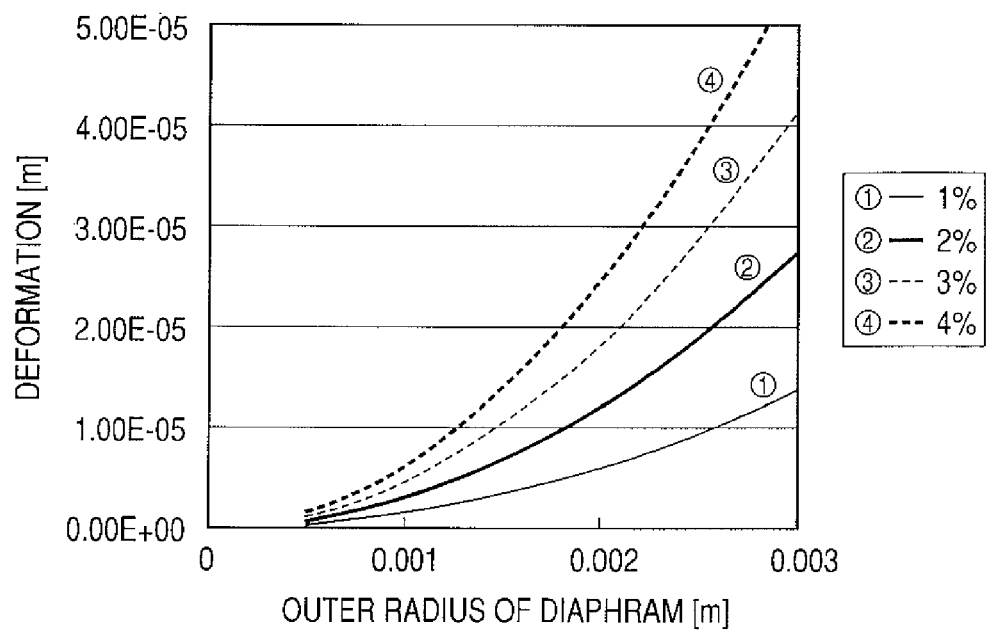
FIG. 22 is a graph of the characteristics illustrating the displacement of the diaphragm for each gas concentration when only the outer diameter is varied without changing the kind and thickness of the film in the combustible gas detector of Example 2 of the present invention.

FIG. 22 illustrates the displacement of the diaphragm for each gas concentration when only the outer diameter is varied without changing the kind and thickness of the film.

It can be appreciated that the larger is the diaphragm, the larger is the deformation. Therefore, detectors switching at different concentrations can be produced by changing the size of the diaphragm.

For example, if the detectors with diaphragms having external diameters of 2.5 mm, 3.5 mm, 4.5 mm, and 5.5 mm are disposed, a change in the concentration can be recognized at four steps.

EXAMPLE 3

Example 3, is a constitution example of a fuel cell system equipped with the combustible gas detector of the present invention.

This Example is described in the case where hydrogen is used as fuel and air is used as an oxidizer in the fuel cell system, but the present invention is not limited to the case where hydrogen and air are used.

Figure 23:
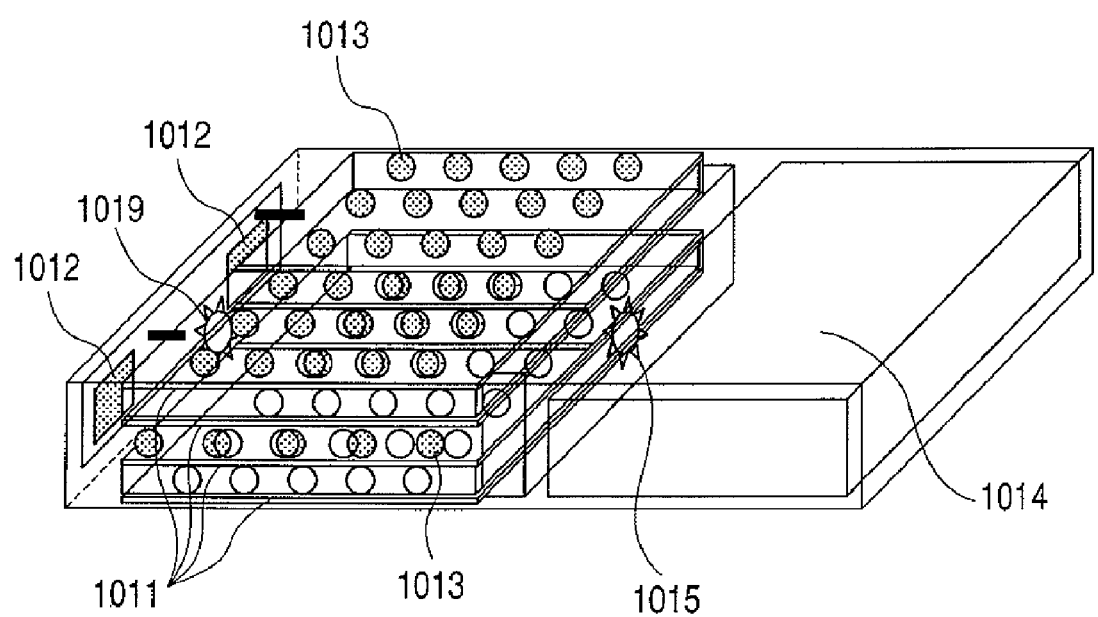
FIG. 23 is a general perspective view illustrating a fuel cell system in Example 3 of the present invention.

FIG. 23 is a general perspective view illustrating a fuel cell system of this Example.

Figure 24:
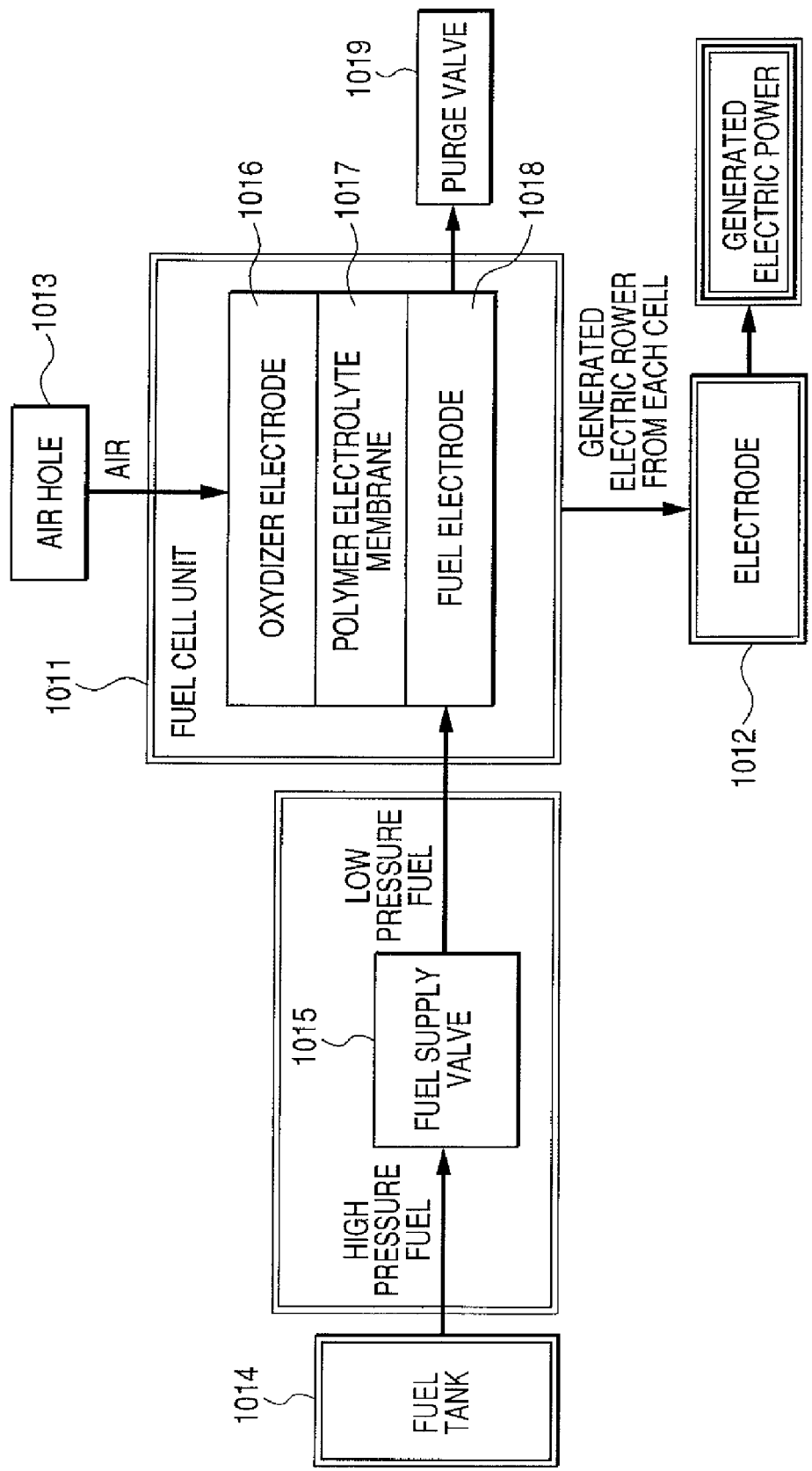
FIG. 24 is a schematic view illustrating the system of the fuel cell in Example 3 of the present invention.
Figure 25:
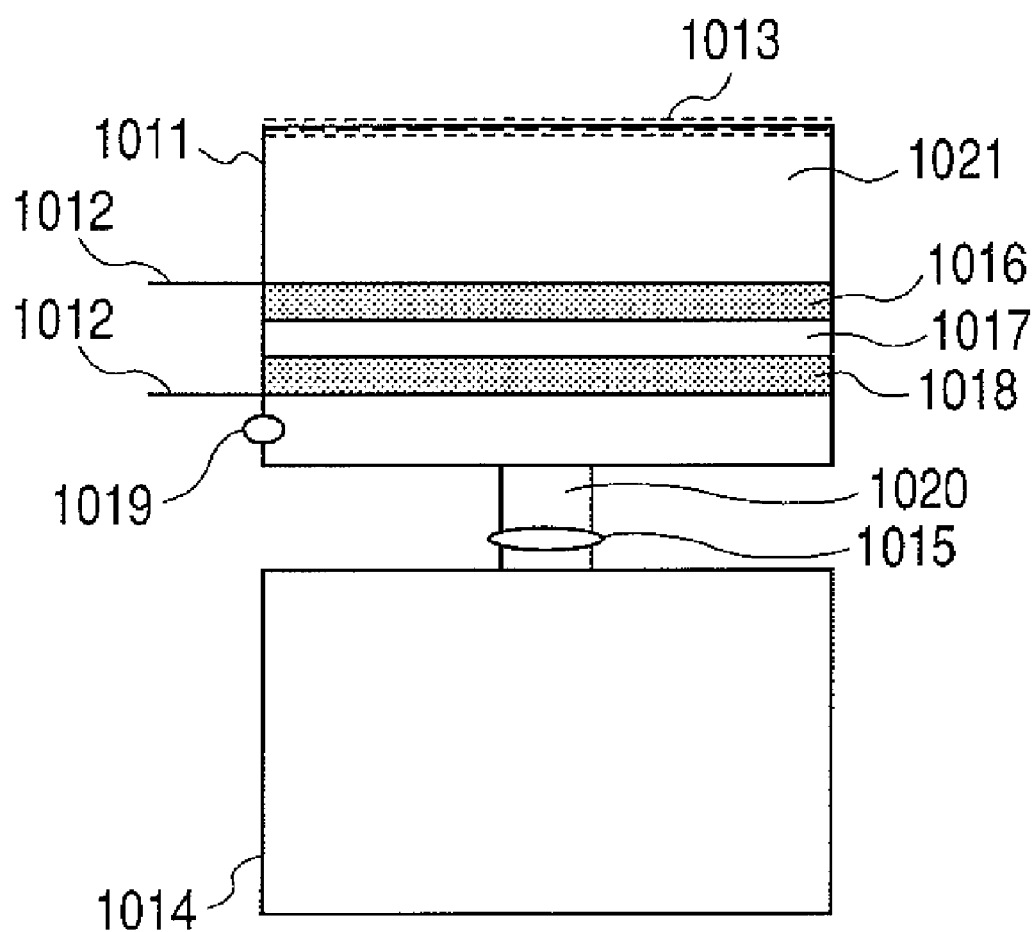
FIG. 25 is a schematic view illustrating the system of the fuel cell in Example 3 of the present invention.

FIGS. 24 and 25 are schematic views illustrating a fuel cell system of this Example.

The external dimensions of the fuel cell are 50 mm×30 mm×10 mm, which are almost the same as the size of lithium ion battery typically used in a compact digital camera.

Because the fuel cell here is small and integrated in this way, it is easy to incorporate it into a portable device.

The fuel cell used in this Example has vent holes 1013 to take in fresh air on the upper and lower surfaces as well as side surfaces so that oxygen to be used for reaction as an oxidizer can be taken in from fresh air.

These holes also allow generated water to emit as vapor and release the heat generated by the reaction to the outside.

In addition, the inside of the fuel cell is provided with a fuel cell 1011 including oxidizer electrode 1016, polyelectrolyte film 1017, and fuel electrode 1018.

The fuel cell includes these elements, fuel tank 1014 for storing the fuel, and the fuel supply valve 1015, which connects the fuel tank with the fuel electrodes of each cell and controls the fuel flow.

When the fuel supply valve 1015 is opened, hydrogen stored in the tank is supplied through the fuel channel 1020 to the fuel electrode 1018.

In the meantime, fresh air is taken in from the vent holes 1013 and supplied to the oxidizer electrodes 1016 through oxidizer channel 1021. Catalysts, such as platinum, are provided respectively on the oxidizer pole 1016 and the fuel electrode 1018 with polyelectrolyte film 1017 of the fuel cell in-between, and the electrochemical reaction occurs.

The electricity generated by the reaction is supplied to a small electric apparatus from the electrodes 1012.

In this reaction, the fuel and the oxidizer are ordinarily not mixed, but reacted at the respective electrode. When the electrolyte film or the channel is damaged, however, the fuel leaks out, fresh air enters the fuel channel, and the fuel leaks out of the fuel channel.

Accordingly, is this Example, a combustible gas detector shown in Example 1 or Example 2 is disposed in at least either one of the fuel channel or the oxidizer channel.

When a combustible gas detector detects a fuel leak, the detector notifies the user about the leakage, stops power generation, and/or terminates the fuel supply.

In particular, the combustible gas detector here can be used as a switch, and the ON/OFF switching of the detector can directly open/close the fueling valve 1015. In addition, this combustible gas detector can be constituted so that it is more readily switched as the temperature of the external environment is elevated. Thus, the fuel cell can be more safely operated. The system may be provided with a purge valve 1019 for purging at the start-up time, shut-down time, or during the operating of the fuel cell. The combustible gas detector of the present invention can also be disposed in the fuel channel 1020 or the discharge port from the purge valve 1019. In that configuration, the combustible gas detector can control the timing to open/close the purge valve 1019 and flow volume of the purge valve 1019 by monitoring the concentration of the gas.

According to the present invention, there are provided a combustible gas detector with a low level of noise, a high-speed response, and low power consumption, which enables miniaturization, a process for producing the combustible gas detector, and a fuel cell system equipped with the combustible gas detector.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application Laid-Open No. 2006-216472, filed Aug. 9, 2006, which is hereby incorporated by reference herein in its entirety.

What is claimed is:

1. A combustible gas detector for detecting a combustible gas, comprising:
    a catalyst for reaction with the combustible gas;
    a first displacement unit including a flexible member which is displaced with catalytic combustion caused by the reaction of the catalyst with the combustible gas; and
    electrical contacts which are switched by displacement of the flexible member in the first displacement unit,
    wherein the flexible member in the first displacement unit is one of a diaphragm and a cantilever, and
    wherein the one of the diaphragm and the cantilever includes one of a laminate formed of a plurality of materials having different thermal expansion coefficients and a shape-memory alloy.

2. A combustible gas detector for detecting a combustible gas, comprising:
    a catalyst for reaction with the combustible gas;
    a first displacement unit including a flexible member which is displaced with catalytic combustion caused by the reaction of the catalyst with the combustible gas; and
    electrical contacts which are switched by displacement of the flexible member in the first displacement unit,
    wherein the flexible member in the first displacement unit is one of a diaphragm and a cantilever, and
    wherein the one of the diaphragm and the cantilever includes a displacement unit which adsorbs the combustible gas and expands with catalytic combustion caused by the reaction of the catalyst with the combustible gas.

3. A combustible gas detector for detecting a combustible gas, comprising:
    a catalyst for reaction with the combustible gas;
    a first displacement unit including a flexible member which is displaced with catalytic combustion caused by the reaction of the catalyst with the combustible gas;
    electrical contacts which are switched by displacement of the flexible member in the first displacement unit; and
    a second displacement unit including a flexible member which is displaced by temperature to a direction opposite to a displacement direction of the flexible member in the first displacement unit,
    wherein the second displacement unit is provided with the first displacement unit through a heat insulating layer.

4. A combustible gas detector array, comprising a plurality of combustible gas detectors, each of the detectors comprising:
    a catalyst for reaction with the combustible gas;
    a first displacement unit including a flexible member which is displaced with catalytic combustion caused by the reaction of the catalyst with the combustible gas; and
    electrical contacts which are switched by displacement of the flexible member in the first displacement unit,
    wherein the flexible members in the plurality of the detectors are different in one of length, width, and thickness.

5. The combustible gas detector according to claim 1, wherein the diaphragm constitutes a partition wall which the combustible gas cannot penetrate and which is provided between the catalyst and an electrical contact.

6. The combustible gas detector according to claim 1, wherein a heat conduction member is provided between the first displacement unit and the catalyst.

7. The combustible gas detector according to claim 1, further comprising a second displacement unit having no catalyst and including a flexible member having the same displacement characteristics by temperature as the first displacement unit, wherein the second displacement unit is provided so that the second displacement unit can be displaced to the same direction as a displacement direction of the first displacement unit.

8. A combustible gas detector array, comprising:
   a first combustible gas detector including a combustible gas detectors according to claim 1, and
   a second combustible gas detector having no a catalyst and including a flexible member which is displaced by temperature and an electrical contact switchable by the displacement of the flexible member,
   wherein the first combustible gas detector and the second combustible gas detector are arranged in one of a parallel state and a stacked state.

9. A combustible gas detector array, comprising a combustible gas detector according to claim 1 arranged in plurality.

10. The combustible gas detector according to claim 2, wherein the diaphragm constitutes a partition wall which the combustible gas cannot penetrate and which is provided between the catalyst and an electrical contact.

11. The combustible gas detector according to claim 2, wherein a heat conduction member is provided between the first displacement unit and the catalyst.

12. The combustible gas detector according to claim 2, further comprising a second displacement unit having no catalyst and including a flexible member having the same displacement characteristics by temperature as the first displacement unit, wherein the second displacement unit is provided so that the second displacement unit can be displaced to the same direction as a displacement direction of the first displacement unit.

13. A combustible gas detector array, comprising:
   a first combustible gas detector including a combustible gas detectors according to claim 2, and
   a second combustible gas detector having no a catalyst and including a flexible member which is displaced by temperature and an electrical contact switchable by the displacement of the flexible member,
   wherein the first combustible gas detector and the second combustible gas detector are arranged in one of a parallel state and a stacked state.

14. A combustible gas detector array, comprising a combustible gas detector according to claim 2 arranged in plurality.

15. The combustible gas detector array according to claim 4, wherein the catalysts in the plurality of the detectors are different in one of kind, amount, and disposed position.

* * * * *